(12) United States Patent
Ouchi (10) Patent No.: US 6,176,873 B1
(45) Date of Patent: Jan. 23, 2001

(54) STENT FOR ENDOSCOPE (75) Inventor: Teruo Ouchi, Saitama-ken (JP)

(73) Assignee: Asahi Kogaku Kogyo Kabushiki Kaisha, Tokyo (JP)

( * ) Notice: Under 35 U.S.C. 154(b), the term of this patent shall be extended for 0 days.

(21) Appl. No.: 09/094,823

(22) Filed: Jun. 15, 1998

(30) Foreign Application Priority Data

Jun. 25, 1997 (JP) .................................................. 9-167819

(51) Int. Cl.$^7$ .................................................. A61F 2/06
(52) U.S. Cl. ........................................ 623/1.22; 623/1.15
(58) Field of Search .................................. 623/1.12, 1.22, 623/1.15; 604/7, 8, 107; 606/193, 194, 198, 200

(56) References Cited

U.S. PATENT DOCUMENTS

| 4,592,341 | | 6/1986 | Omagari et al. . | |
|---|---|---|---|---|
| 4,655,771 | * | 4/1987 | Wallsten | 623/1 |
| 4,921,484 | * | 5/1990 | Hillstead | 604/104 |
| 4,998,539 | | 3/1991 | Delsanti . | |
| 5,234,458 | * | 8/1993 | Mefais | 606/200 |
| 5,354,310 | * | 10/1994 | Garnic et al. | 606/198 |
| 5,405,380 | * | 4/1995 | Gianotti et al. | 606/195 |
| 5,476,505 | * | 12/1995 | Limon | 623/1 |
| 5,496,277 | * | 3/1996 | Termin et al. | 604/104 |
| 5,522,790 | * | 6/1996 | Moll et al. | 600/24 |
| 5,626,602 | * | 5/1997 | Gianotti et al. | 606/198 |
| 5,649,906 | * | 7/1997 | Gory et al. | 604/53 |

\* cited by examiner

Primary Examiner—Bruce Snow
(74) Attorney, Agent, or Firm—Greenblum & Bernstein, P.L.C.

(57) ABSTRACT

A stent includes a mesh tube so constituted that a diameter thereof is contracted when axially extended, while the diameter thereof returns to its original diameter when not axially extended. A cap is provided to a first axial end of the mesh tube for bundling the first axial end of the mesh tube. The cap has a through hole connecting an interior and an exterior of the mesh tube. A tail tube is provided to a second axial end of the mesh tube so that the tail tube and the mesh tube form a continuous path. The tail tube bundling the second axial end of the mesh tube.

6 Claims, 9 Drawing Sheets

STENT FOR ENDOSCOPE

BACKGROUND OF THE INVENTION

The present invention relates to a stent for an endoscope.

When a biliary stricture occurs, a biliary duct is narrowed to cause a clogging in a biliary duct. In such case, the flow of a bile is prevented, which may cause an icterus.

A stent is used to treat a stricture including the above mentioned biliary stricture. The stent is carried by an endoscope and inserted into a narrow portion of the annular organ (such as a biliary duct), thereby to widen the narrow portion. The stent is left in the narrow portion of the annular organ.

A conventional stent includes an expandable tube (for example, a mesh tube made of steel wires). When the stent is inserted into the annular organ, the expandable tube expands thereby to widen the narrow portion of the annular organ.

However, such conventional stent has a disadvantage such that, once the stent is left in the annular organ, it is difficult to remove the stent from the annular organ.

Further, a recently developed stent has projections which engage a surface of the annular organ, so as to prevent the stent from slipping out of the annular organ. It is further difficult to remove such stent from the annular organ.

In some cases, it is necessary to replace the stent with new one (particularly when the stent is clogged). Thus, there is strong demand of a stent which can be easily removed from an annular organ.

SUMMARY OF THE INVENTION

It is therefore an object of the present invention to provide a stent which can be easily removed from an annular organ.

According to an aspect of the present invention, there is provided a stent including a mesh tube so constituted that a diameter thereof is contracted when axially extended, while the diameter thereof returns to its original diameter when not axially extended. A cap is provided to a first axial end of the mesh tube for bundling the first axial end thereof. The cap has a through hole which connects an interior and an exterior of the mesh tube. A tail tube is provided to a second axial end of the mesh tube so that the tail tube and the mesh tube form a continuous path. The tail tube bundles the second axial end of the mesh tube.

On inserting the stent into an annular organ, a pusher tube is inserted through the continuous path (the tail tube and the mesh tube) so that the tip of the pusher tube abuts the cap. When the cap is pushed by the pusher tube, the mesh tube is extended in axial direction. With this, the diameter of the mesh tube can be contracted. Further, during the insertion of the stent into the annular organ, the mesh tube is axially extended due to the force applied by the pusher tube and a friction between the mesh tube and the annular organ. That is, the diameter of the mesh tube is contracted during the insertion of the stent. Thus, the stent can be smoothly inserted into the annular organ.

Further, as constructed above, the stent can be removed from an annular organ by pulling the tail tube. Thus, the stent can be easily removed from the annular organ.

In a particular arrangement, the tail tube has a catch hole formed at a certain distance from the mesh tube. With this, it is possible to hook the catch hole (using a hooking device or the like) and to pull the tail tube. Thus, the stent can be further easily removed from the annular organ.

It is preferred to provide a string to the tail tube. One end of the string is fixed to the tail tube, while the other end of the string is a free end. Optionally, a knot can be formed on the free end of the string. With this, it is possible to hook the knot (using a hooking device or the like) and to pull the string. Thus, the stent can be further easily removed from the annular organ.

Preferably, the cap includes an inner ring portion and an outer ring portion. The inner and outer ring portions are so constituted that a periphery of the first axial end of the mesh tube is sandwiched between the inner and outer ring portions. Optionally, it is possible to provide a connecting ring for connecting the mesh tube and the tail tube. Further, an inner diameter of the cap is smaller than an inner diameter of the tail tube. With this, when the pusher tube is inserted through the tail tube and the mesh tube, the tip of the pusher tube abuts a surface around the through hole of the cap.

According to another aspect of the present invention, there is provided a stent including a mesh tube so constituted that a diameter thereof is contracted when axially extended, while the diameter thereof returns to its original diameter when not axially extended. A cap is provided to a first axial end of the mesh tube for bundling the first axial end thereof. The cap has a through hole which connects an interior and an exterior of the mesh tube. The mesh tube is bundled at a second axial end thereof. A string is provided to the second axial end.

Accordingly, it is possible to remove the stent from the annular organ by pulling the string. Thus, the stent can be easily removed from the annular organ.

In a preferred embodiment, one end of the string is fixed to the tail tube, while the other end of the string is a free end. Further, a knot is formed on the free end of the string. With this, it is possible to hook the knot (using a hooking device or the like) and to pull the string. Thus, the stent can be further easily removed from the annular organ.

DESCRIPTION OF THE PREFERRED EMBODIMENT

A first embodiment of the present invention is described.

Figure 1:
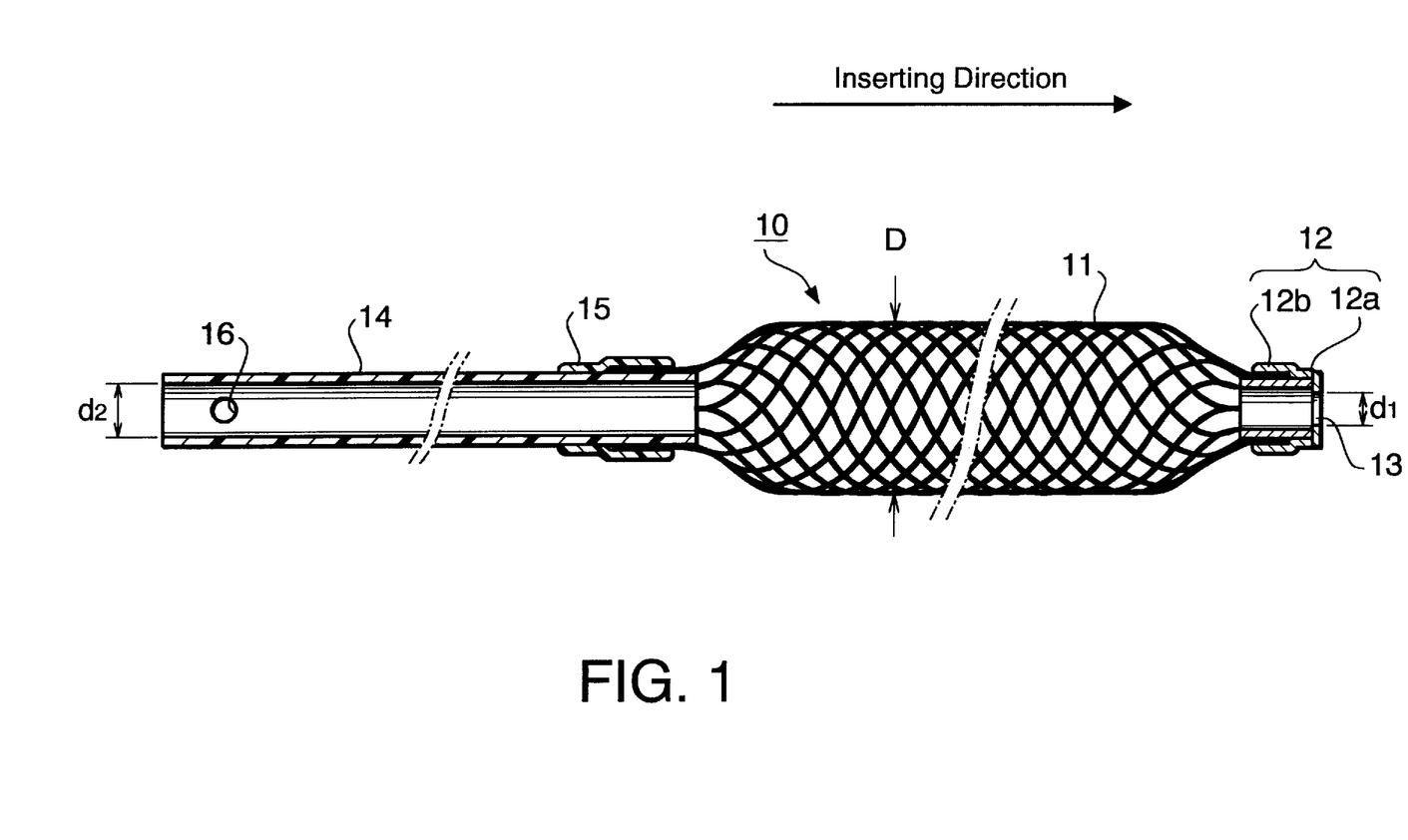
FIG. 1 is a sectional view of a stent according to a first embodiment.

FIG. 1 is a sectional view of a stent 10 according to the first embodiment. The stent 10 includes a mesh tube 11 made by netting wires (such as stainless wires or the like). Hereinafter, a 'head end' and a 'tail end' of the stent 10 are defined with respect to the inserting direction shown by an arrow in FIG. 1.

The mesh tube 11 is so constituted that the diameter of the mesh tube 11 is contracted when the mesh tube 11 is axially extended, while the diameter of the mesh tube 11 returns to its original diameter D when the mesh tube is not axially extended.

A cap 12 is provided to a head end of the mesh tube 11 for bundling the mesh tube 11. The cap 12 includes inner and outer ring portions 12*a* and 12*b* which are fixed to each other at the tip thereof. The ring portions 12*a* and 12*b* sandwich a periphery of the head end of the mesh tube 11 therebetween. The diameter of the cap 12 is smaller than the original diameter D of the mesh tube 11, so that the diameter of the head end of the mesh tube 11 is smaller than the original diameter D. A through hole 13 is formed in the center of the inner tube 12*a*, which connects the interior and the exterior of the mesh tube 11.

A tail tube 14 is provided to a tail end of the mesh tube 11 so that the tail tube 14 and the mesh tube 11 form a a continuous path. In order to fix the tail tube 14 to the mesh tube 11, a fixing ring 15 is fixed (by welding) to the outer surface of the tip of the tail tube 14. The fixing ring 15 urges the tail end of the mesh tube 11 to the outer surface of the tail tube 14. The fixing ring 15 and the tip of the tail tube 14 sandwich a periphery of the tail end of the mesh tube 11. In this state, the diameter of the tail end of the mesh tube 11 is smaller than the original diameter D. Further, the inner diameter d2 of the tail tube 14 is larger than the inner diameter d1 of the through hole 13 of the cap 12. It is also possible to unitarily form the fixing ring 15 with the tail tube 14.

The tail tube 14 has a catch hole 16 formed at a tail end thereof. As described below, after the stent 10 is left in the annular organ, it is possible to remove the stent 10 from the annular organ by hooking the catch hole 16*a* with a forceps or the like.

Figure 2:
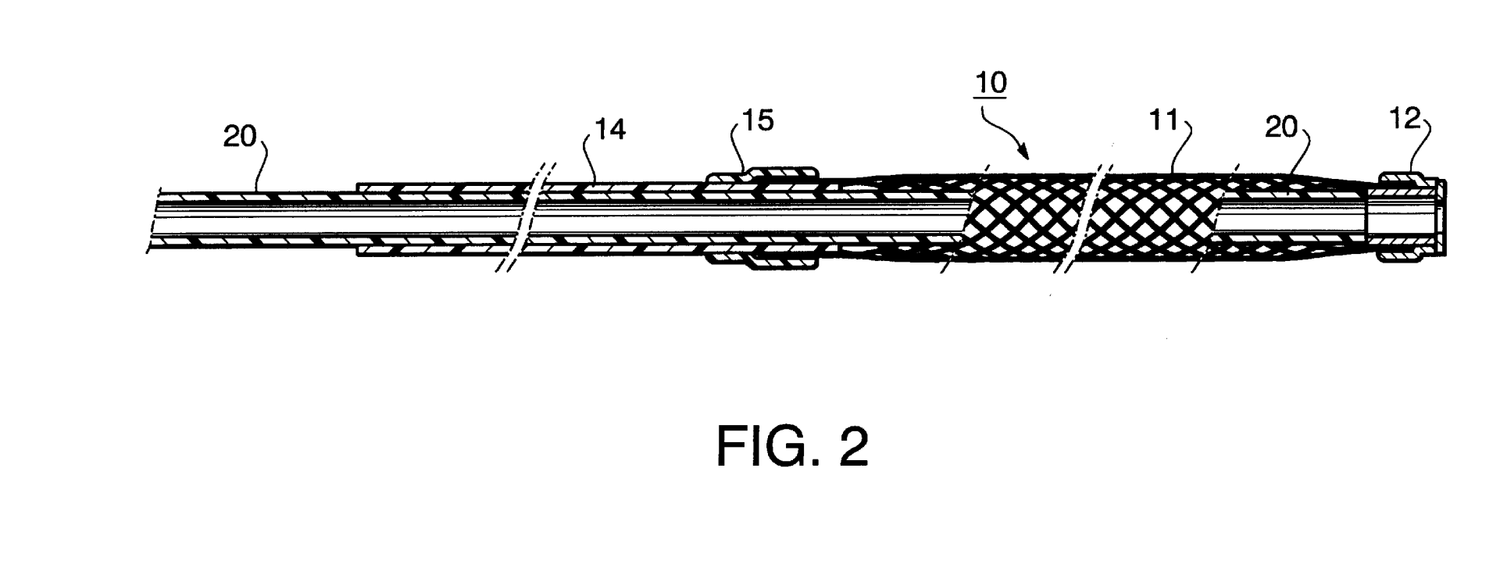
FIG. 2 is a sectional view of the stent of FIG. 1 and a pushing tube.

A pusher tube 20 is used to push the stent 10 into the annular organ. As shown in FIG. 2, a pusher tube 20 includes a flexible tube made of synthetic resin. The pusher tube 20 is inserted into the tail tube 14 and the mesh tube 11 so that the tip of the pusher tube 20 abuts the cap 12. Since the inner diameter of the cap 12 d1 is larger than the inner diameter d2 of the tail tube 14, the tip of the pusher tube 20 abuts a surface of the cap 12 surrounding the through-hole 13. When the cap 12 is pushed by the pusher tube 12 while holding the tail tube 14, the mesh tube 11 is axially extended as shown in FIG. 2. That is, the diameter of the mesh tube 11 is contracted.

Figure 3:
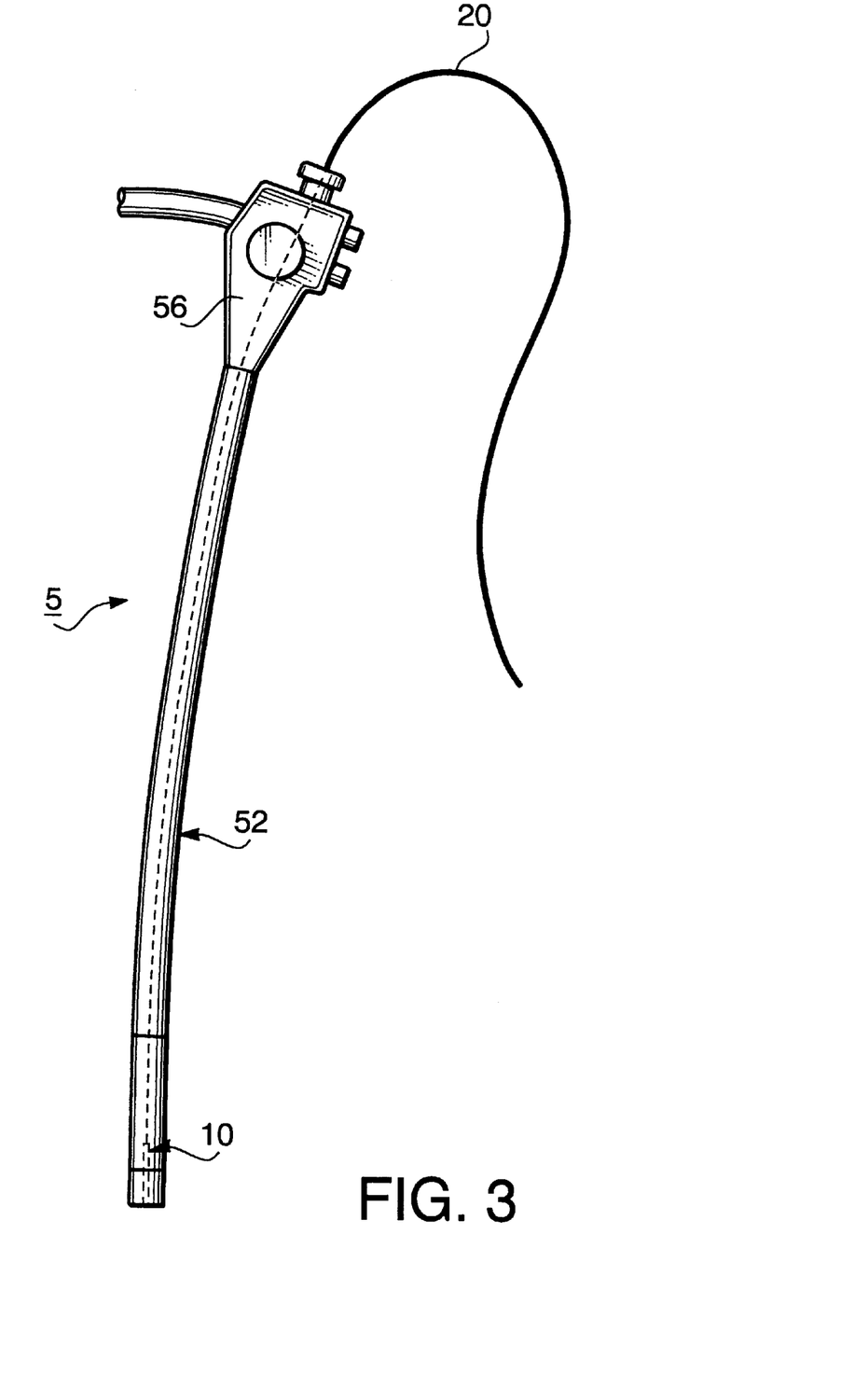
FIG. 3 is a side view of an endoscope carrying the stent of FIG. 1.

FIG. 3 is a schematic view showing an endoscope 5 in which the stent 10 is set. The stent 10 is inserted into a channel 54 (FIG. 4) of an insertion tube 52 of the endoscope 5. Further, the stent 10 is set to a head end of the insertion tube 52. In this state, the pusher tube 20 extends to an operating portion 56 of the endoscope 5 and further extends to the exterior of the endoscope 5. With this, an operator is able to operate the pusher tube 20. The setting of the stent 10 (in the endoscope 5) is performed before the insertion tube 52 is inserted into a human body.

Figure 4:
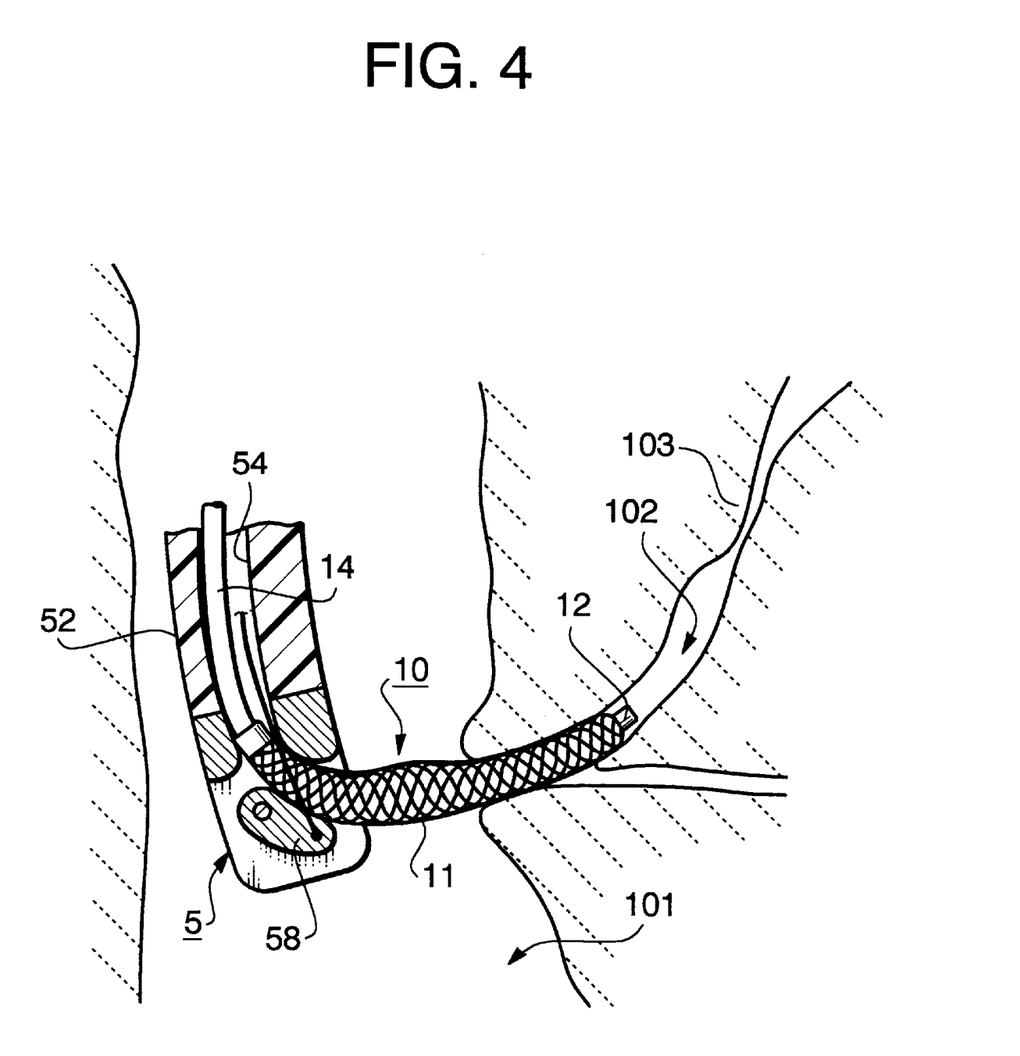
FIG. 4 is a schematic view illustrating the stent of FIG. 1, which is inserted into a annular organ.

FIG. 4 illustrates the stent 10 being inserted through a duodenum 101 into a biliary duct 102. An operator inserts an insertion tube 52 of the endoscope 5 into the duodenum 101. Then, the operator pushes the pusher tube 20 so as to push the stent 10 into the biliary duct 102. The bending direction of the stent 10 can be controlled by a retractor 58 provided to the tip of the insertion tube 52. The retractor 58 is located in the vicinity of an exit opening of the channel 54. The retractor 58 is swingable and is remotely operated by the operator via a wire. When the pusher tube 20 is pushed while the stent 10 is bent, the tail tube 14 is urged to an inner surface of the channel 54. That is, the mesh tube 11 is axially extended due to the force applied by the pusher 20 and a friction between the mesh tube 11 and the tail tube 14. Thus, the stent 10 can be inserted into the biliary duct 102 in a state that the diameter of the mesh tube 11 is contracted.

There is a possibility that the diameter of the mesh tube 11 is increased during the insertion of the mesh tube 11. Even in such case, the diameter of the mesh tube 11 can be decreased by further pushing the pusher tube 20. It is because the mesh tube 11 is axially extended due to the force applied by the pusher 20 and a friction between the mesh tube 11 and the biliary duct 102.

Figure 5:
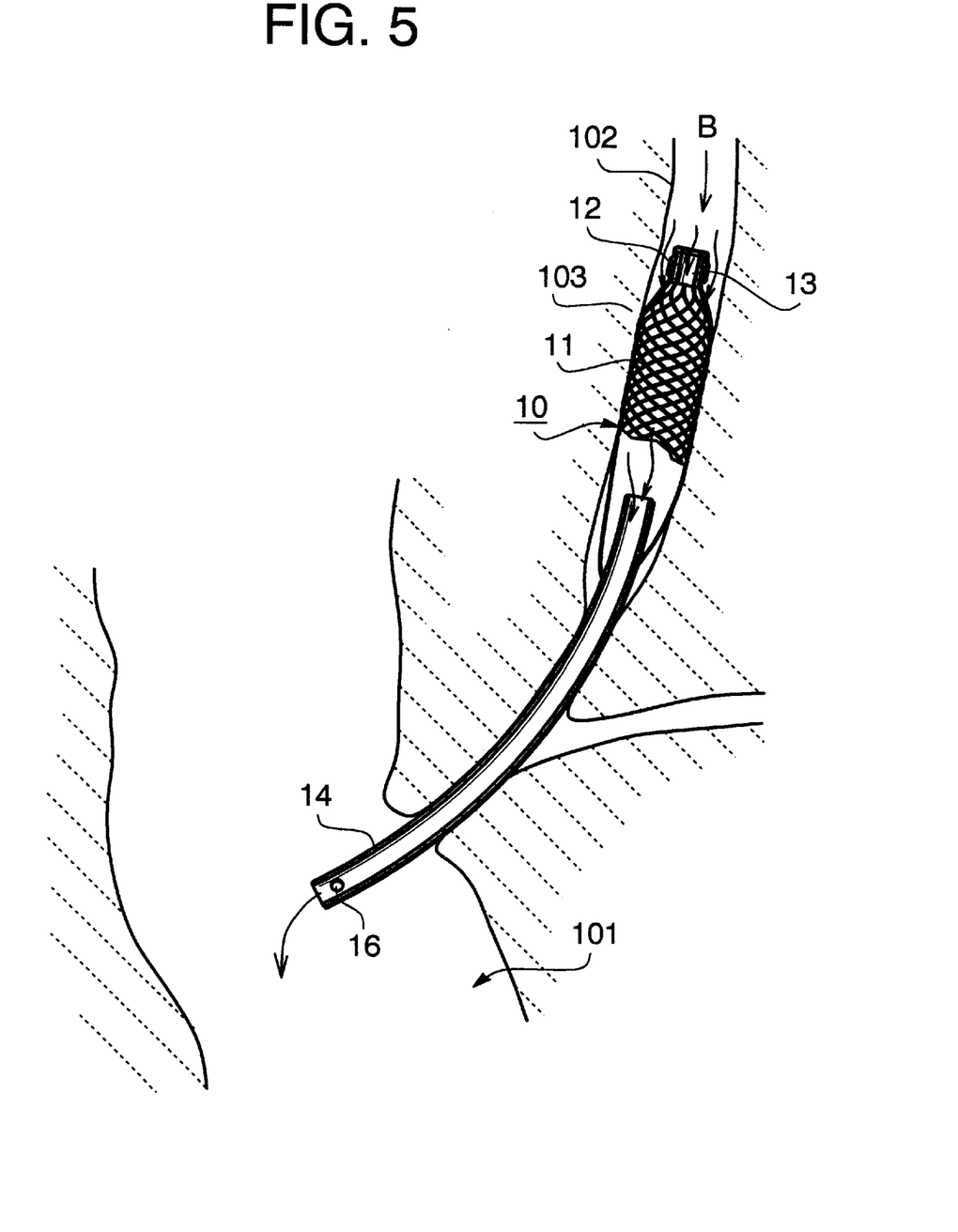
FIG. 5 is a schematic view illustrating the stent of FIG. 1, which is left in the annular organ.

FIG. 5 illustrates the stent 10 being left in the biliary duct 102. After the mesh tube 11 reaches a narrow portion 103 of the biliary duct 102, the operator retracts the pusher tube 20 and the endoscope 5 from the duodenum 101. The stent 10 is left in the narrow portion 103 and is expanded (returns to its original diameter) so as to urge the inner surface of the narrow portion 103 outward. Thus, the narrow portion 103 is widened. The length of the tail tube 14 is so set that the tail end of the tail tube 14 is located in the duodenum 101 when the stent 10 is in the narrow portion 103 of the biliary duct 102. In this embodiment, the length of the tail tube 14 is set from 20 to 80 cm. When the stent 10 is left in the biliary duct 102, a bile B flows (through a through hole 13 of the cap 12 and openings among the wires the mesh tube 11) into the mesh tube 11 and the tail tube 14. The bile B further flows through the mesh tube 11 and the tail tube 14 and flows in the duodenum 101.

On removing the mesh tube 11, it is possible to hook the catch hole 16 by means of a forceps (not shown) or a hooking device (not shown) and to pull the tail tube 14. As the tail tube 14 is pulled (while the mesh tube 11 contacts the biliary duct 102), the mesh tube 11 is axially extended by a certain amount. Thus, the diameter of the mesh tube 11 decreases. With this, the stent 10 can be smoothly removed from the biliary duct 102.

As described above, according to the first embodiment, the stent 10 can be easily removed from the biliary duct 102. Thus, in case the mesh tube 11 is clogged or the like, it is possible to easily replace the stent 10 with new one.

In the first embodiment, it is alternatively possible to set the stent 10 in the endoscope 5 after the insertion tube 52 is inserted into the duodenum 101.

The second embodiment of the present invention is described.

Figure 6:
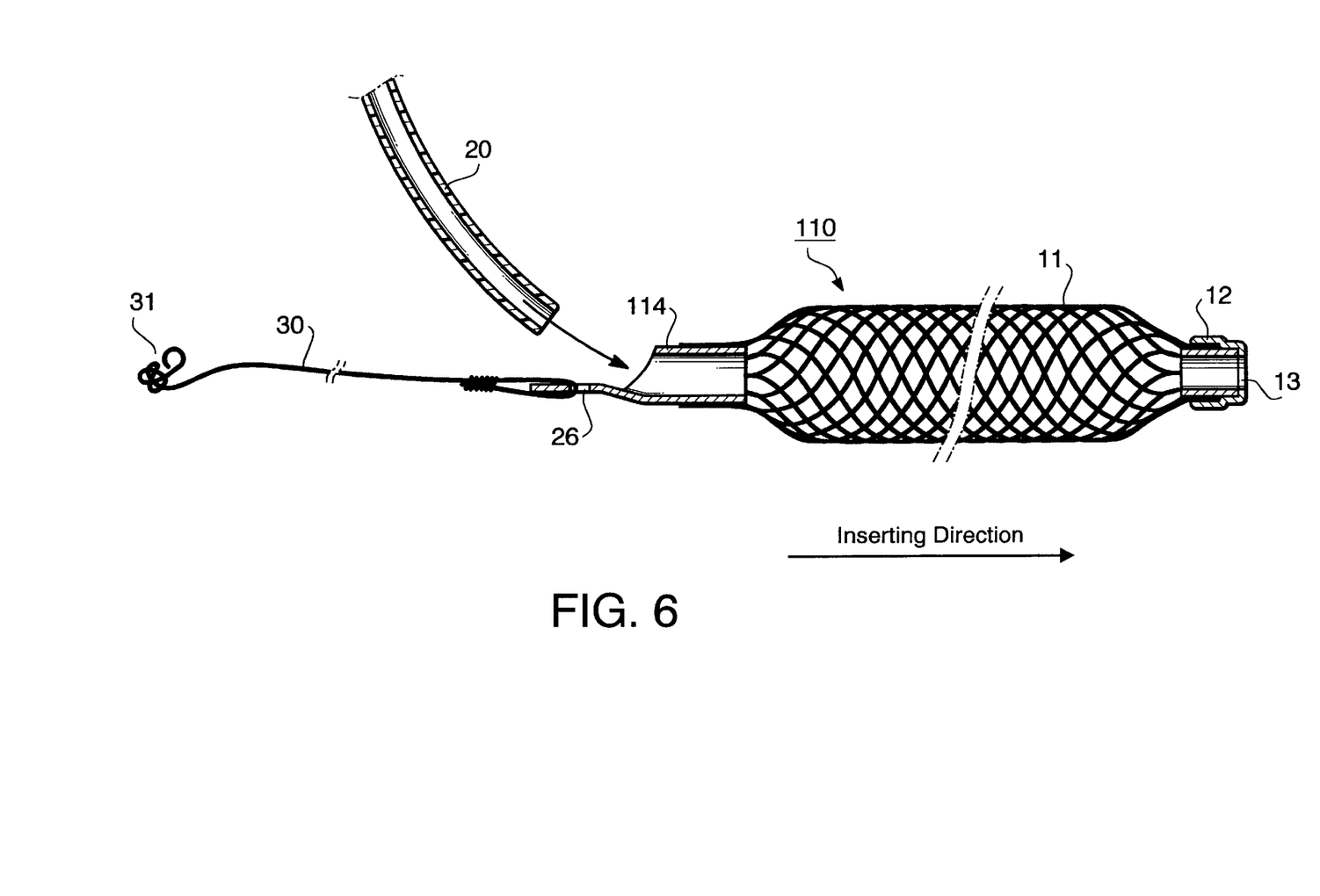
FIG. 6 is a sectional view of a stent according to a second embodiment.

FIG. 6 is a sectional view of a stent 110 according to the second embodiment. The stent 110 includes the mesh tube 11 and the cap 12 which are same as those of the first embodiment. The stent 110 further includes a short tail tube 114 made of a rigid material (instead of the tail tube 14 of the first embodiment). A string 30 is fixed to the tail end of the tail tube 14. One end of the string 30 is fixed to the tail tube 114, while the other end of the string is a free end. In order to fix the string 30 to the tail tube 114, a hole 26 is formed at a tail end of the tail tube 114 through which the string 30 is inserted. A knot 31 is formed on the free end of the string 30. As in the first embodiment, the pusher tube 20 is inserted into the tail tube 114 and the mesh tube 11.

Figure 7:
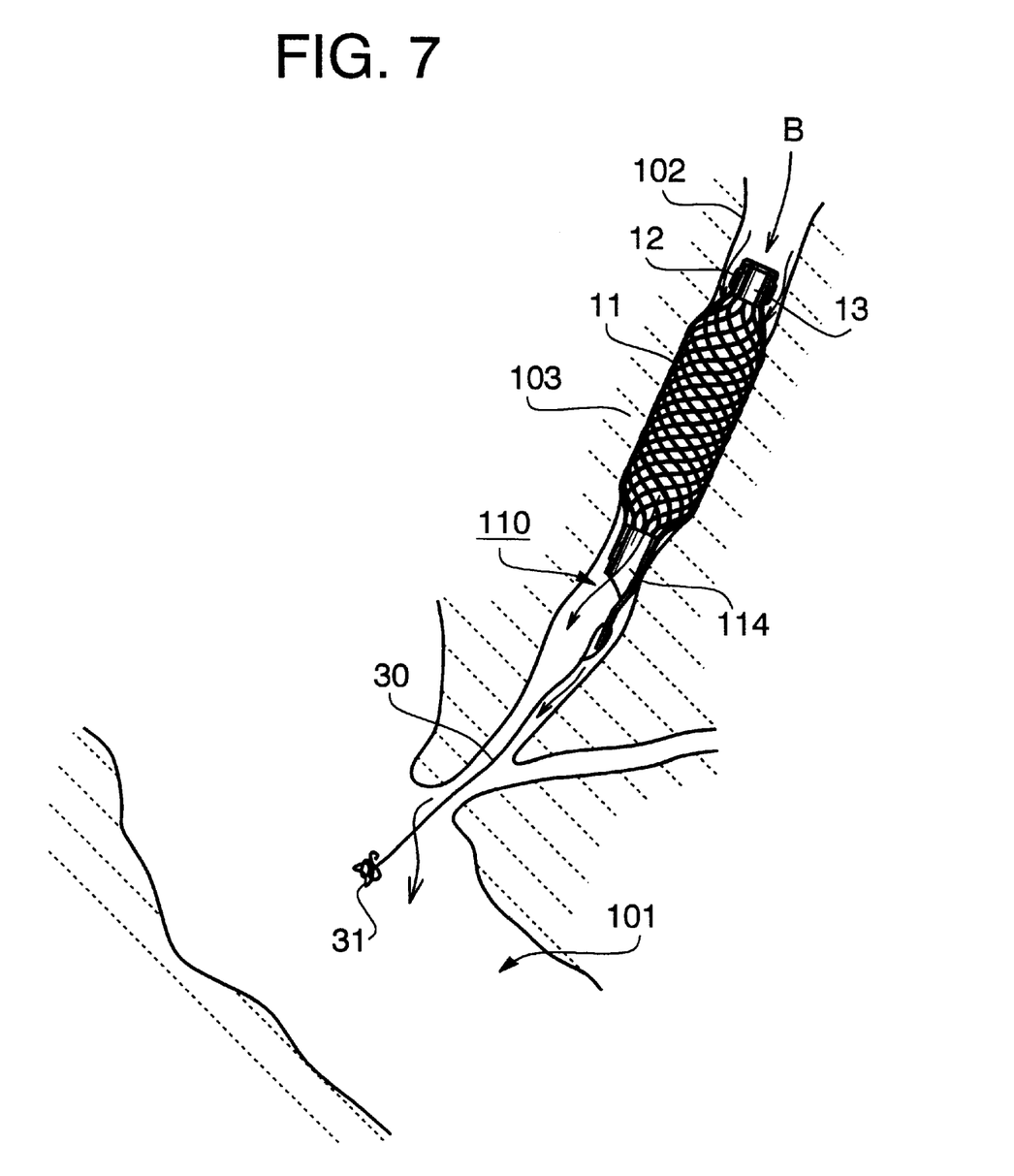
FIG. 7 is a schematic view illustrating the stent of FIG. 6, which is inserted into a annular organ.

FIG. 7 illustrates the stent 110 being inserted through the duodenum 101 into the biliary duct 102. The stent 110 is inserted into the biliary duct 102 (by means of the pusher tube 20) in a similar manner to the first embodiment. The stent 110 is left in the biliary duct 102 and is expanded so as to widen the inner surface of the narrow portion 103. In this state, the bile B flows into the mesh tube 11 and the tail tube 14. The bile B flows through the mesh tube 11 and the tail tube 14 and flows in the duodenum 101.

Figure 8:
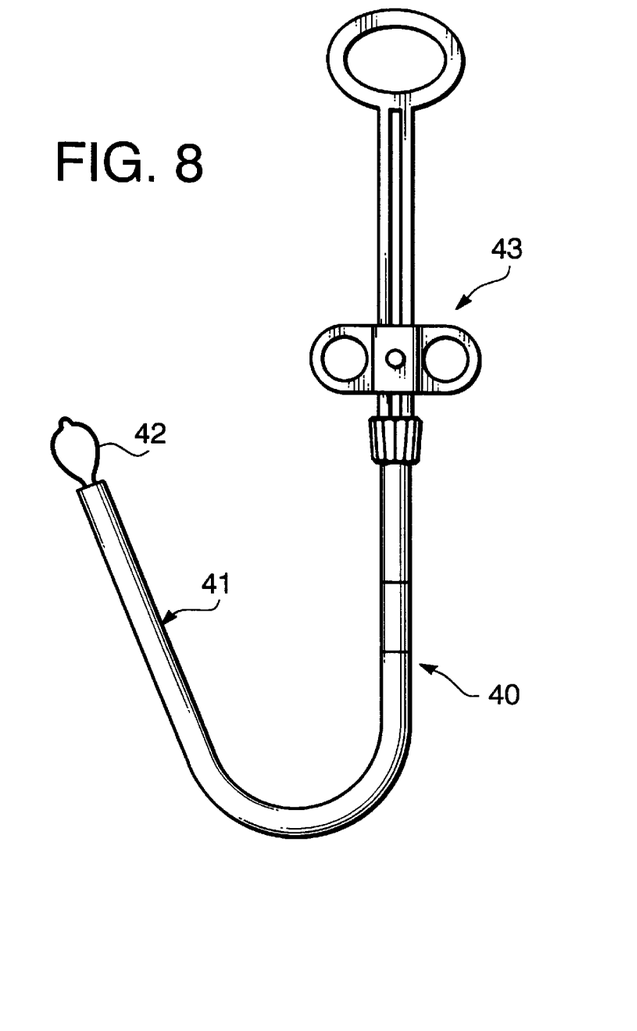
FIG. 8 is a side view of a device for removing the stent from the annular organ.

The length of the string 30 is so set that the knot 31 is located in the duodenum 101 when the mesh tube 11 is in the narrow portion of the biliary duct 102. Thus, it is possible to remove the stent 110 from the biliary duct 102, by hooking the knot 31 by means of a forceps (not shown) or a hooking device (not shown) and by pulling the string 30. FIG. 8 shows a snare 40 which can be used to remove the stent 110. The snare 40 includes a wire loop 42, a sheath 41 covering the wire loop 42 and an operating portion 43 for moving the wire loop 42. The wire loop 42 is able to grab the knot 31 of the string 30.

As described above, according to the second embodiment, the stent 110 can be easily removed from the biliary duct 102.

The third embodiment of the present invention is described.

Figure 9:
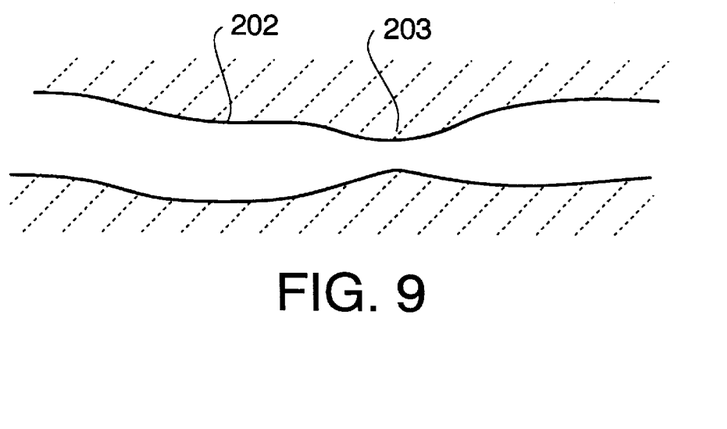
FIG. 9 is a schematic view of a FIG. 7 is a schematic view illustrating a narrow portion of a blood vessel.

FIG. 9 is a schematic view of a narrow portion 203 of a blood vessel 202. The narrow portion 203 is made of cholesterol adhered to the surface of the blood vessel 202. The stent 210 of the third embodiment is intended to treat such blood vessel 202.

Figure 10:
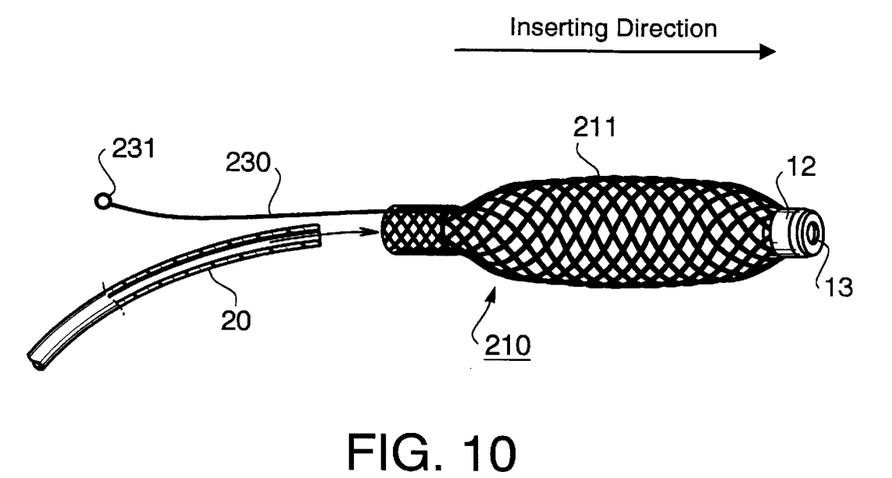
FIG. 10 is a sectional view of a stent according to a third embodiment.

FIG. 10 is a side view of the stent 210 of the third embodiment. The stent 210 includes a mesh tube 211. A head end of the mesh tube 211 is bundled by the cap 12 which is the same as that of the first embodiment. A tail end of the mesh tube 211 is netted in a smaller diameter. Other structure of the mesh tube 211 is same as the mesh tube 11 of the first embodiment. A string 230 is provided to the tail end of the mesh tube 211. One end of the string 230 is fixed to the tail end of the mesh tube 211, while the other end of the string 230 is a free end. A knot 231 is formed on the free end of the string 230. As in the first and second embodiments, the pusher tube 20 is inserted in the mesh tube 211.

Figure 11:
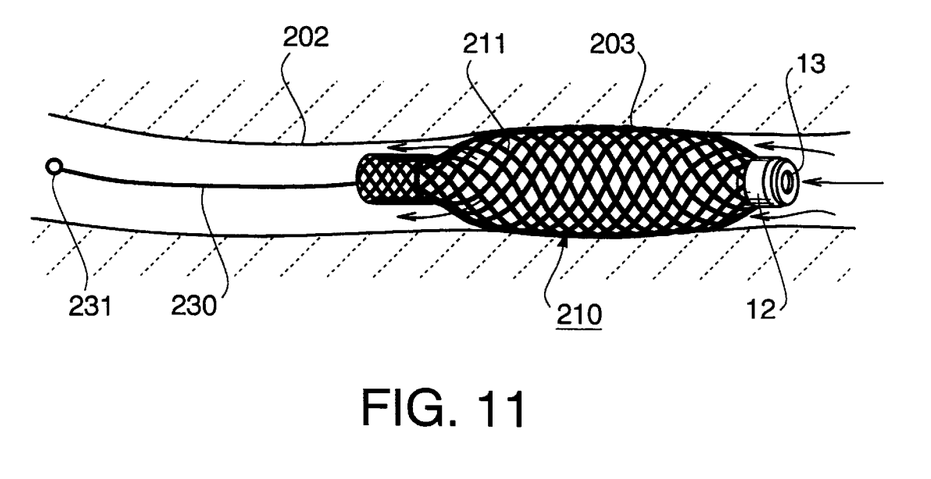
FIG. 11 is a schematic view illustrating the stent of FIG. 10, which is inserted into a annular organ.

The stent 210 is inserted into the blood vessel 202 in a similar manner to the first and second embodiments. When the stent 210 is left in the blood vessel 202, the mesh tube 211 is expanded to urge the blood vessel 202 to enlarge the diameter of the blood vessel 202. In this state, blood flows through the openings of wires of the mesh tube 211 and the through hole 13 of the cap 12. On removing the stent 210 from the blood vessel 202, it is possible to hook the knot 231 and pull the string 230.

As described above, according to the third embodiment, the stent 210 can be easily removed from the blood vessel 202.

The stent described in the first through third embodiments can be used for widening a trachea or other purpose.

Although the structure and operation of a stent for an endoscope is described herein with respect to the preferred embodiments, many modifications and changes can be made without departing from the spirit and scope of the invention.

The present disclosure relates to subject matters contained in Japanese Patent Application No. HEI 09-167819, filed on Jun. 25, 1997, which is expressly incorporated herein by reference in their entirety.

What is claimed is:

1. A stent comprising:

a mesh tube having a diameter that is contracted from an original size when axially extended, the diameter returning to the original size when not axially extended;

a cap provided to a first axial end of said mesh tube, said cap bundling said first axial end of said mesh tube, said cap having a hole connecting an interior and an exteiror of said mesh tube; and a tail tube provided to a second axial end of said mesh tube so that said tail tube and said mesh tube form a continuous path, said tail tube bundling said second axial end of said mesh tube, said tail tube having a catch hole formed at a predetermined distance from said mesh tube.

2. The stent according to claim 1, further comprising a string provided to said tail tube, wherein one end of said string is fixed to said tail tube, while the other end of said string is a free end.

3. The stent according to claim 2, wherein a knot is formed on said free end of said string.

4. The stent according to claim 1, said cap including an inner ring portion and an outer ring portion, wherein said inner and outer ring portions are so constituted that a periphery of said first axial end of said mesh tube is sandwiched between said inner and outer ring portions.

5. The stent according to claim 1, further comprising a connecting ring fixed to said tail tube, which connects said mesh tube and said tail tube.

6. The stent according to claim 1, wherein each of said cap and said tail tube has a diameter smaller than an original outer diameter of said mesh tube.

* * * * *